United States Patent [19]

Elmore

[11] 4,436,586

[45] Mar. 13, 1984

[54] METHOD OF PRODUCING KRAFT PULP USING AN ACID PREHYDROLYSIS AND PRE-EXTRACTION

[75] Inventor: Carl L. Elmore, Glen Falls, N.Y.

[73] Assignee: Kamyr, Inc., Glen Falls, N.Y.

[21] Appl. No.: 341,627

[22] Filed: Jan. 22, 1982

[51] Int. Cl.³ .................. D21C 1/04; D21C 1/06; D21C 3/02
[52] U.S. Cl. ........................ 162/19; 162/65; 162/82; 162/90; 435/163; 435/165
[58] Field of Search ............ 162/19, 90, 76, 65, 162/237, 82; 435/161, 163, 165

[56] References Cited

U.S. PATENT DOCUMENTS

| | | | |
|---|---|---|---|
| 3,097,987 | 7/1963 | Sloman | 162/17 |
| 3,311,530 | 3/1967 | Justus et al. | 162/19 |
| 3,380,883 | 4/1968 | Richter et al. | 162/19 |
| 3,413,189 | 11/1968 | Backlund | 162/29 |
| 4,071,399 | 1/1978 | Prough | 162/16 |
| 4,094,742 | 6/1978 | Bellamy | 435/165 |
| 4,104,113 | 8/1978 | Sherman et al. | 162/19 |
| 4,155,806 | 5/1979 | Mannbro | 162/65 |
| 4,174,997 | 11/1979 | Richter | 162/19 |
| 4,342,831 | 8/1982 | Faber et al. | 435/163 |

FOREIGN PATENT DOCUMENTS

WO81/01154  4/1981  PCT Int'l Appl. ............ 435/163
222549  9/1924  United Kingdom ............ 435/165

OTHER PUBLICATIONS

"Billerud Pioneers Prehydrolysis-Kraft Pulping"; reprint from Pulp & Paper International, Dec. 1967.
"Continuous Prehydrolysis-Kraft Cooking" by Annergren et al., 1965.

Primary Examiner—Steve Alvo
Attorney, Agent, or Firm—Cushman, Darby & Cushman

[57] ABSTRACT

A method for producing both kraft pulp and alcohol from hardwood chips or the like. The chips are subjected to mild acid prehydrolysis following by mild caustic pre-extraction. The withdrawn hydrolystate has insufficient furfural to inhibit microorganism growth, and both the hexose and pentose sugars in the hydrolysate are fermented to ultimately produce ethanol, butanol, or the like. The chips - after caustic pre-extraction - are subjected to a sulphate cook, and wash, and the resultant pulp is kraft pulp and even has viscosity and tear strength characteristics more desirable than that of conventional kraft pulp. The pulp can be subjected to oxygen delignification, and achieve a higher K number in fewer subsequent bleaching stages than conventional kraft pulp.

20 Claims, 5 Drawing Figures

METHOD OF PRODUCING KRAFT PULP USING AN ACID PREHYDROLYSIS AND PRE-EXTRACTION

BACKGROUND AND SUMMARY OF THE INVENTION

Prehydrolysis of comminuted cellulosic fiber material, such as wood chips, is a well known technique both for ultimately producing pulp or for ultimately producing alcohols. For instance in the conventional prehydrolysis of wood chips before kraft cooking thereof (e.g. see U.S. Pat. No. 3,380,883) the chips are subjected to high temperature (e.g. 170° C.) water, or to a sulfuric acid solution, hydrolysate containing carbohydrate material is removed, and the hydrolysate is conventionally burned to produce steam.

In the conventional production of alcohols, biomass is subjected to acid hydrolysis to break down the cellulose component of the biomass into hexose and pentose sugars with subsequent fermentation of the hexose sugars. Since the same component of the feed material that is utilizable for producing alcohol is under conventional procedures the same component necessary for pulp having good strength properties, the two procedures have conventionally been mutually exclusive. Where prehydrolysis is practiced for pulp production, only dissolving pulp is conventionally produced [dissolving pulp is utilized for the manufacture of rayon or plastics]. Effective production of kraft pulp, suitable for manufacture of paperboard or suitable for oxygen delignification and bleaching to produce paper, has heretofore not been practical. The hydrolysate has usually been removed with the black liquor and burned, and even if not burned (see U.S. Pat. No. 4,174,997) has not been considered suitable for alcohol production. Conversely, when biomass is treated with acid hydrolysis for alcohol production, the biomass residue (as distinct from the hydrolysate) is not suitable for kraft cooking.

According to the present invention, it is possible to treat comminuted cellulosic fiber material so that the carbohydrate material therein is removed in appropriate form to be utilized for the production of alcohols (such as ethanol and butanol), while at the same time the bulk of the comminuted cellulosic fiber material can be subjected to sulfate cooking and can produce a kraft pulp. The pulp produced not only has strength properties within the desired range for the making of paperboard, paper, or the like, but actually has a higher viscosity and higher tear strength than conventional pulps. This is advantageous in that it is possible to effect oxygen bleaching of the pulp to a lower Kappa number with fewer subsequent bleaching stages. Additionally, by practicing the invention it is possible to use a lower active alkali charge in the kraft cooking stage than is conventional.

According to one aspect of the present invention, a method of producing carbohydrate material and kraft pulp from comminuted cellulosic fiber material is provided. The basic steps are: (a) Subjecting the comminuted cellulosic fiber material to mild acid prehydrolysis. The term "mild acid prehydrolysis" as used in the present specification and claims means prehydrolysis treatment sufficient to effect removal of a high percentage of the carbohydrate material (particularly pentosans) from the cellulosic fiber material (alone or in conjunction with the following caustic extraction step to be hereinafter described), while not substantially adversely affecting the cellulosic component of the material the conditions being an acid concentration of, or equivalent to, about 0.2–0.5% $H_2SO_4$, and a temperature of about 120° C. or less. (b) Subjecting the prehydrolysized comminuted cellulosic fiber material to mild caustic pre-extraction. The term "mild caustic pre-extraction" as used in the present specification and claims means caustic pre-extraction under conditions effective to remove a large percentage of the carbohydrate materials (particularly pentosans) from the comminuted cellulosic fiber material (alone or in conjunction with the previously described mild acid hydrolysis), while not substantially adversely affecting the strength or yield characteristics of the bulk of the cellulosic fiber material which is ultimately subjected to kraft cooking the caustic extraction conditions being a concentration of, or equivalent to, about 0.5–4% NaOH, at a temperature of about 60°–90° C. (c) Removing hydrolysate having carbohydrate material from the comminuted cellulosic material while practicing the prehydrolysis and pre-extraction steps. The hydrolysate is primarily useful as a feed material for the production of alcohol, and by subjecting it to neutralization, clarification, fermentation, and distillation both the pentose and hexose sugars therein will ultimately be turned into alcohol such as ethanol or butanol. And, (d) effecting kraft (sulfate) cooking of the prehydrolysized, pre-extracted comminuted cellulosic fiber material to produce kraft pulp. The kraft pulp produced has a substantially higher viscosity (and tear strength) than the same pulp produced from the same comminuted cellulosic fiber material and under substantially identical kraft cooking conditions, but without prehydrolysis and pre-extraction.

The method may also comprise the further step of effecting oxygen delignification of the kraft pulp, with ultimate bleaching thereof to the desired brightness. Steps (a) through (d) are practiced so that the delignified kraft pulp produced has a lower Kappa number than such pulp produced from the same comminuted cellulosic fiber material and under substantially identical kraft cooking and oxygen delignification conditions, but without prehydrolysis and pre-extraction. The method is particularly useful where the cellulosic fiber material is chips or sawdust of hardwood, and is desirably practiced so that the prehydrolysis and pre-extraction are effected in a first vessel, and kraft cooking is practiced in a second vessel. The acid prehydrolysis is desirably practiced with a concurrent flow of material and acid, while the caustic extration is desirably practiced with a countercurrent flow of caustic and material.

The apparatus utilizable in practicing the method of producing carbohydrate material and kraft pulp according to the invention includes many conventional components, such as a chips bin, steamer, high pressure feeder, and continuous digester. The primary addition to the conventional components is the provision of a "first" vertical vessel between the steaming vessel and high pressure feeder on one hand, and the digester on the other. The first vessel includes a material inlet at the top, an acid hydrolysis zone, hydrolysate withdrawal screens, and a countercurrent caustic pre-extraction zone adjacent the bottom. Treated material is fed from the bottom of the first vessel to the top of the digester. Acid for the prehydrolysis may be added in a recirculation loop within the prehydrolysis zone of the first vessel, or can be added at the level tank supplying makeup water to the chips feed to the high pressure feeder. The alkali is added in a recirculation loop associated with the pre-extraction stage, and the recirculating liquid is cooled to maintain the desired pre-extraction temperature (which is normally substantially below the prehydrolysis temperature).

The alcohol production aspects of the present invention are independently utilizable (i.e. even where the production of kraft pulp is not desired or practical), and can maximize alcohol yield from biomass material. For instance where "low quality" (from the pulp production standpoint) cellulosic fiber material is utilized, such as bagesse, after particlization and slurrying the material is fed directly to the hydrolysis-extraction vessel. The vessel in this case is substantially identical to the first vessel of the process and apparatus described above. The acid hydrolysis and caustic extraction steps are practiced at acid and caustic concentrations, and at temperature and residence time conditions, sufficient to effect treatment of the hemicellulose in the biomass material to effect separation of pentose and hexose sugars therefrom into a hydrolysate having insufficient furfural to substantially inhibit fermentation microorganism growth, while not substantially hydrolysizing the cellulose in the biomass. The cellulose component may be washed and dewatered, and subsequently burned for its energy content, while the hydrolysate is removed from the hydrolysized and extracted biomass. The hydrolysate is neutralized and clarified and is subjected to fermentation so that the pentose and hexose sugars therein are fermented. Alcohol is then produced from the fermented hexose and pentose sugars.

The acid hydrolysis and caustic extraction parameters when practicing the method of alcohol production described in the previous paragraph may be slightly different than those utilized in the aspect of the method which results in the production of kraft pulp. For instance the acid concentration can be in the range of about 0.3–2% $H_2SO_4$, or the equivalent, and the caustic concentration can be about 1.5–6% NaOH or equivalent. The hydrolysis conditions can be from about 105° C. to 135° C., with about 120° C. being preferred, while the extraction temperature conditions can be from about 60° C.–120° C.

It is the primary object of the present invention to provide for the treatment of comminuted cellulosic fiber material to maximize the removal of suitable carbohydrate material therefrom, while preferably at the same time maintaining the material in condition suitable for the kraft cooking thereof to produce a kraft pulp having satisfactory (and even improved for some parameters) strength properties. This and other objects of the invention will become clear from an inspection of the detailed description of the invention, and from the appended claims.

DETAILED DESCRIPTION OF THE PREFERRED EMBODIMENT

Figure 1:
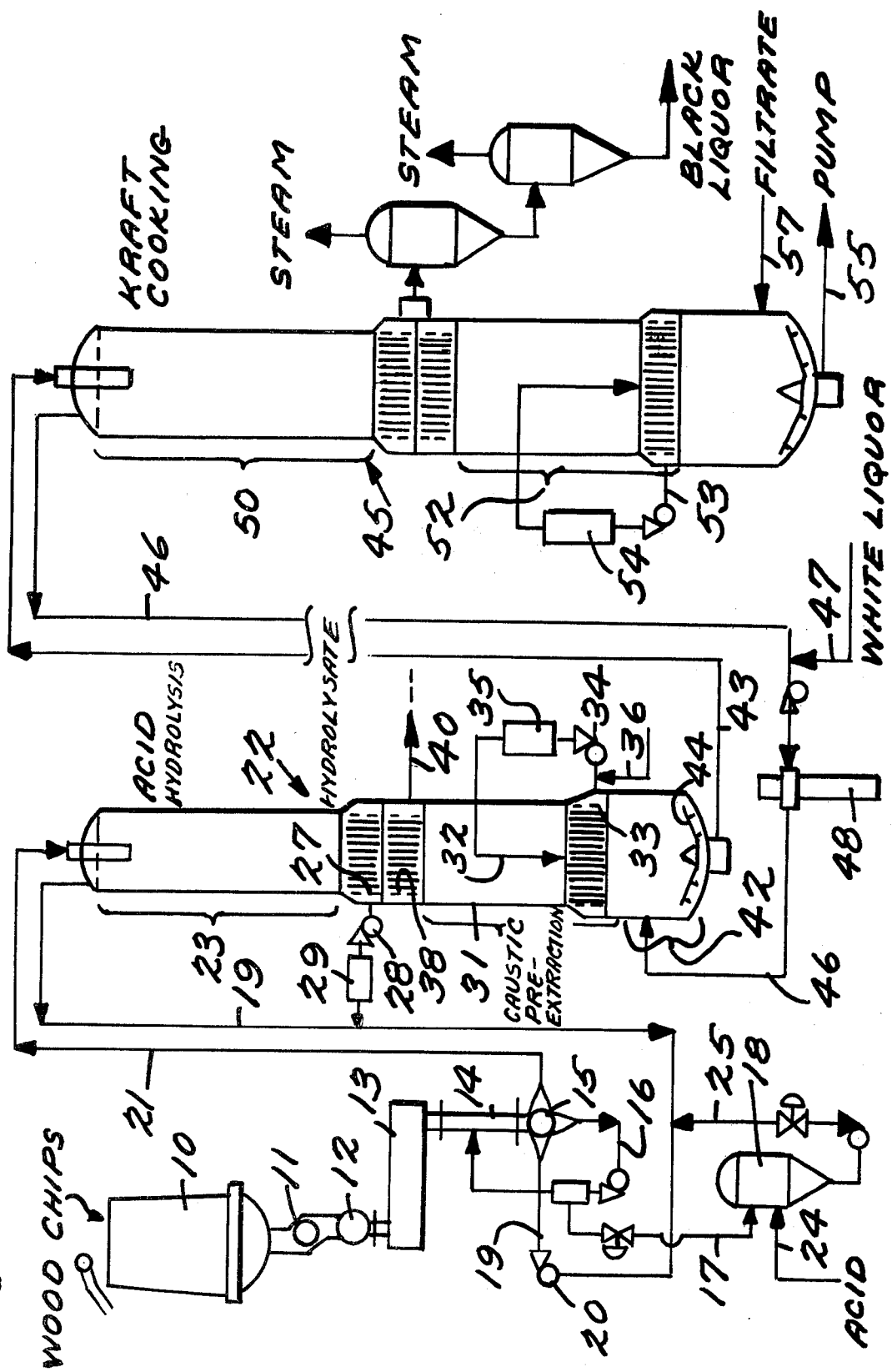
FIG. 1 is a schematic view of exemplary apparatus according to the present invention for the production of carbohydrate material and kraft pulp from comminuted cellulosic fiber material.

Exemplary apparatus according to the present invention is illustrated schematically in FIG. 1. Utilizing the exemplary apparatus it is possible to produce carbohydrate material in the form of a hydrolysate that may be further acted upon to produce alcohol, such as ethanol, butanediol, or butanol. Apparatus for treating the hydrolysate is illustrated schematically in FIG. 2. The apparatus of FIG. 1 further is capable of producing kraft pulp, which may be further oxygen delignified or otherwise acted upon to produce a wide variety of high quality paper products.

Conventional components of the apparatus of FIG. 1 include a chips bin 10 into which a supply of wood chips, such as hardwood (e.g. maple) or softwood (e.g. pine) chips (including pin chips and like small size wood components), sawdust, or the like are deposited. The chips are fed via a chips meter 11 and low pressure feeder 12 to a horizontal steaming vessel 13, for ultimate disposition into the entry conduit 14 leading to the high pressure feeder 15. Alternatively, a bin steaming arrangement could be provided, with a feed therefrom directly into the conduit 14. A low pressure recirculation line 16 from the high pressure feeder 15 returns liquid withdrawn from the high pressure feeder 15 back to the entry conduit 14, with overflow therefrom being provided through line 17 into level tank 18. Circulating liquid in high pressure feed line 19 is pressurized by pump 20, and fed through high pressure discharge line 21 to the top of a first treatment vessel 22, with liquid being returned from the top of vessel 22 to line 19.

First vessel 22 is a vertical vessel capable of being pressurized in which mild acid prehydrolysis and mild caustic pre-extraction of the wood chips are accomplished. The acid prehydrolysis takes place in a concurrent flow between acid and chips in a top portion 23 of vessel 22. In the embodiment illustrated in FIG. 1, acid is added to the chips for the concurrent flow at the level tank 18, as illustrated by inlet line 24. The concentration of the acid in the liquid in level tank 18 is capable of precise control, and the liquid with desired acid concentration from tank 18 is fed via line 25 to return line 19 from vessel 22. The mild acid keeps the high pressure feeder 15 free of most contaminants, and the long flow path of the acid in contact with the chips (from high pressure feeder 15 to the top of vessel 22), as well as the concurrent flow in the upper portion 23 of vessel 22, effects acid prehydrolysis of the chips.

Typical prehydrolysis conditions that are utilized in the practiced in the invention are a concentration of, or equivalent to, about 0.2–0.5% $H_2SO_4$, and a temperature of about 120° C. or less (e.g. about 105° C.–120° C.). In order to maintain the temperature for the acid prehydrolysis at the desired level, liquid at the bottom of the prehydrolysis zone 23 of vessel 22 is withdrawn through screen 27 by pump 28, and then is heated in heater 29 (which may be a steam heater), before ultimate passage to the return line 19. The pressure in the prehydrolysis zone 23 would conventionally be about 200 psig.

The vessel 22 also includes a lower zone 31 in which countercurrent caustic pre-extraction is practiced. A caustic solution is added through central tube 32, and flows upwardly from the area of bottom screen 33 toward the interface with acid prehydrolysis zone 23. Excess caustic solution is withdrawn through bottom screen 33 via pump 34, and is passed through a cooler 35 to return to the central inlet pipe 32. Makeup alkali is added to this flow at line 36. The flow and addition rates, vessel dimensioning, etcetera are designed so that the caustic is substantially spent by the time it reaches the area of middle screen 38. The middle screen 38 is at the area of interface between the concurrent acid prehydrolysis zone 23 and the countercurrent caustic pre-extraction zone 31. Hydrolysate produced both during the acid prehydrolysis and during the caustic pre-extraction flows through middle screen 38 into hydrolysate discharge line 40. The hydrolysate may then be acted on in an appropriate manner, such as utilizing the apparatus illustrated in FIG. 2.

Typical conditions for the mild caustic pre-extraction are a caustic concentration of, or equivalent to, about 0.5-4% NaOH, and a temperature of about 60°-90° C. Because the temperature in the caustic pre-extraction zone 31 is substantially lower than that in the acid prehydrolysis zone 23, the cooler 35 is utilized. The pressure in the caustic pre-extraction zone 31 is not particularly critical, but would be on the order of about 220 psig. Residence times in both zones 23, 31 may be adjusted as necessary depending upon the makeup of the wood chips, capacity of the subsequent digester, etcetera, but normally would be about 60 minutes in each zone.

The prehydrolysized, pre-extracted wood chips are discharged from the bottom zone 42 of the vessel 22 into line 43. A rotating scraper 44 may be provided at this area to facilitate discharge. Line 43 passes to the top of a conventional continuous digester 45, with a return of liquid being provided through line 46 to the bottom zone 42 of vessel 22. White liquor addition takes place in line 46, as indicated by line 47, and additionally the liquid is heated, as by heater 48, so that it is close to cooking temperature when introduced into the top of the digester 45. This is especially desirable since at the bottom of the caustic pre-extraction zone 31 the chips mass will have a relatively low temperature (e.g. on the order of 60°-90° C.).

Figures 2, 3:
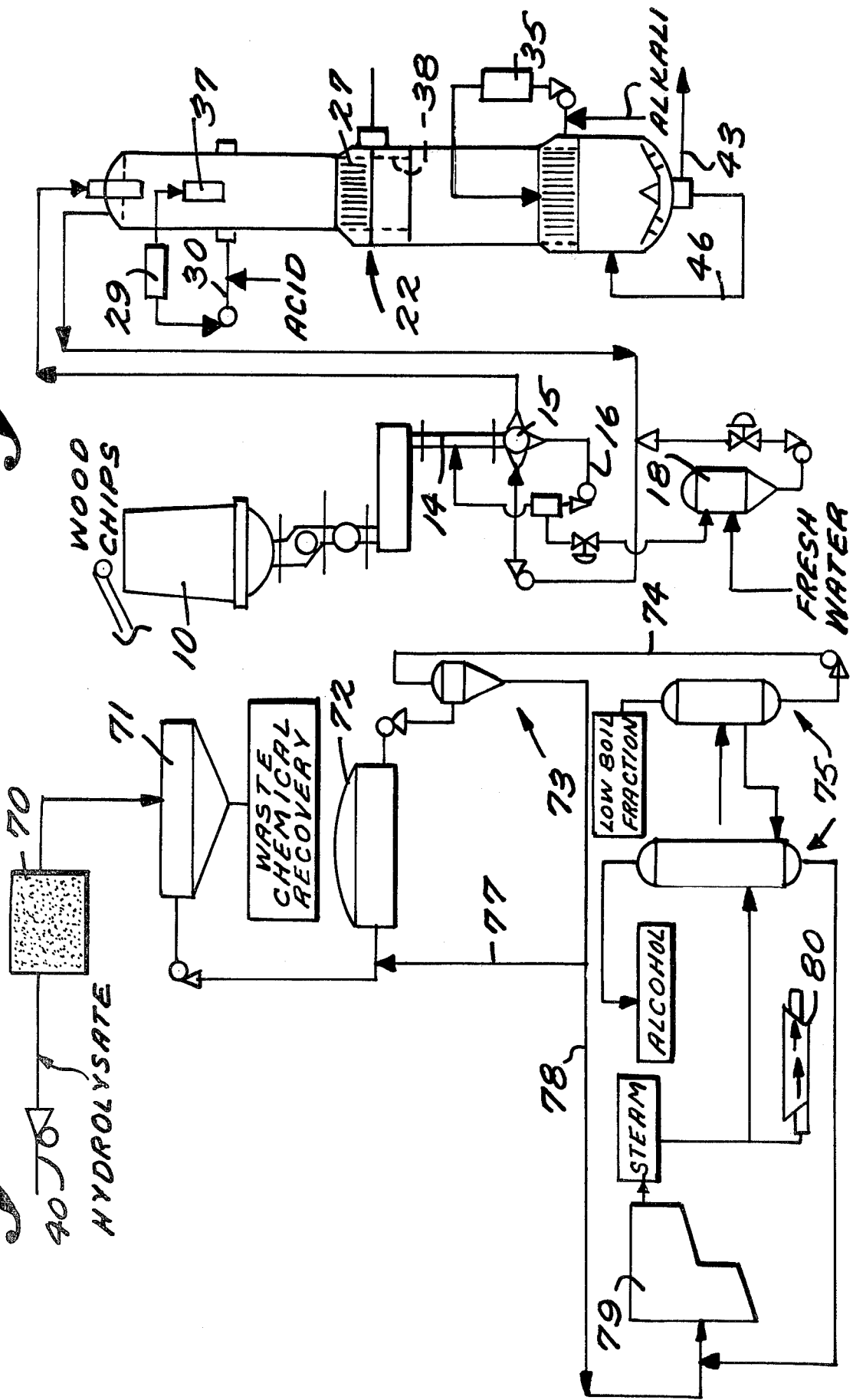
FIG. 2 is a schematic view illustrating the subsequent treatment of the hydrolysate from the apparatus of FIG. 1 for the ultimate production of alcohol therefrom.
FIG. 3 is a schematic view of a modification of the apparatus of FIG. 1, the modification being with respect to the mechanism for the acid introduction for the prehydrolysis step.

The apparatus illustrated in FIG. 3 is substantially identical to that illustrated in FIG. 1, and like reference numerals refer to like components. The only difference of the apparatus of FIG. 3 is in the particular way in which the acid is added for the prehydrolysis. In this case instead of adding the acid at the level tank 18, it is added at a recirculation line 30 leading to the central conduit 37, the heater 29 being provided in the recirculation loop. The hydrolysate withdrawn into line 40 is withdrawn both from screens 27 and 38 in this instance.

In the top portin 50 of continuous digester 45, the chips are subjected to a kraft cook (i.e. a sulfate chemical pulping process). Generally a conventional cooking conditions (e.g. 165° C., 90 minutes residence time, 220 psig pressure) are utilized. However because of removal of organic material by prehydrolysis and caustic pre-extraction, a lower active alkali charge can be utilized in the zone 50. Conventional countercurrent washing takes place in zone 52, the wash liquid being withdrawn through line 53 and heated by heater 54, and kraft pulp is ultimately discharged through line 55 at the bottom of the vessel 45. The pulp withdrawn in line 55 is true kraft pulp, having strength properties comparable to kraft pulp produced by conventional digesters when prehydrolysis and pre-extraction are not practiced. In fact, the pulp produced according to the invention has a greater viscosity, and greater tear strength than conventional kraft pulp, although other strength parameters are slightly lower than conventional (although still within acceptable range). Thus, by practicing the invention it is possible to produce kraft pulp, with a minimum effect upon yield and strength, while at the same time producing a hydrolysate that is suitable for use in the production of alcohol. Thus the maximum amount of high quality product is obtained from a given volume of wood chips, with very little waste or low quality product.

Exemplary results obtainable when practicing the method of the invention, as compared to conventional results, are illustrated in Tables I and II. The hardwood utilized was Northeastern Maple. Hardwood batch A was 31% plus 7 mm thick, batch B was nil plus 7 mm thick, while batch C was low plus 7 mm thick. The softwood used was Southern Pine chips. With the exception of cook number 8, the liquor-to-wood ratios in the prehydrolysis and caustic zones were 2.0 and 2.5, respectively. For batch number 8 the ratios were 3.7 and 3.5, respectively. For all cooks except batches 1 and 2 the liquor-to-wood ratio in the kraft cooking zone was 3.2. For cooks 1 and 2, the ratio was 4.0. No interstage washing was practiced. The pressure maintained in the acid prehydrolysis stage was about 200 psig, while it was about 220 psig in the other stages.

TABLE I

| | HARDWOOD COOKS | | | | | | | |
|---|---|---|---|---|---|---|---|---|
| Cook No. | 1 | 2 | 3 | 4 | 5 | 6 | 7 | 8 |
| Hardwood Batch | A | C | B | C | C | C | C | C |
| Prehydrolysis | None | None | | None | | | | |
| $H_2SO_4$, sol'n. % | | | 1 | | 0.3 | 1.0 | 1.0 | 0.3 |
| Temp, °C. | | | 105 | | 120 | 90 | 90 | 120 |
| Time, min. | | | 60 | | 60 | 90 | 60 | 60 |
| Total solids, % | | | 1.6 | | 1.1 | 0.9 | 0.8 | 0.85 |
| Final pH | | | 1.5 | | 2.0 | 1.7 | 1.7 | 1.7 |
| Caustic Extraction | None | None | None | | | | | |
| NaOH, % on wood | | | | 1.5 | 1.5 | 2.0 | 3.0 | 4.0 |
| Temp, °C. | | | | 60 | 60 | 60 | 60 | 90 |
| Time, min. | | | | 60 | 60 | 60 | 60 | 90 |
| Total solids, % | | | | 1.1 | 1.2 | 1.3 | 1.8 | 2.6 |
| Final pH | | | | 9.4 | 8.8 | 8.7 | 9.9 | 9.2 |
| Ext. Solids Removal | | | | | | | | |

TABLE I-continued

HARDWOOD COOKS

| Cook No. | 1 | 2 | 3 | 4 | 5 | 6 | 7 | 8 |
|---|---|---|---|---|---|---|---|---|
| Hardwood Batch | A | C | B | C | C | C | C | C |
| (% on Wood) | | | | | | | | |
| prehydrolysis stage | | | | | 1.8 | 0.6 | 0.4 | 2.2 |
| extraction stage | | | | 1.9 | 2.1 | 2.1 | 2.6 | 5.8 |
| total | | | | 1.9 | 3.9 | 0.7 | 3.0 | 8.0 |
| Kraft Stage | | | | | | | | |
| AA, % | 15.5 | 15.5 | 16 | 14 | 14 | 14 | 13.2 | 12.8 |
| Max. temp., °C. | 163 | 163 | 157 | 162 | 162 | 162 | 161 | 159 |
| Time temp., min. | 90 | 90 | 60 | 80 | 80 | 80 | 80 | 80 |
| Residual alkali, gpl. | | 7.0 | 9.3 | 3.7 | 5.4 | 7.0 | 6.8 | 8.4 |
| K Number | 15.6 | 15.2 | 16.2 | 15.4 | 11.5 | 12.8 | 14.2 | 11.9 |
| Total yield % | 51 | 52.5 | 47.8 | 52.6 | 48.8 | 50.4 | 51.0 | 46.3 |
| Total rejects % | 3.7 | | 4.6 | 0.9 | 0.4 | 0.5 | 1.3 | 0.7 |
| Viscosity (cp) | 53 | 59.5 | 122 | 59.2 | 73 | 66.7 | 66 | 76.7 |
| Pentosan, % | 21.2 | | 11.3 | 22.3 | 19.5 | 20.5 | 22.5 | 14.0 |
| Paper Properties 400 CSF | | | | | | | | |
| PFI revs | 300 | 200 | 550 | 300 | 200 | 100 | 150 | |
| Burst | 28 | 30 | 32 | 31 | 31 | 28 | 32 | |
| Tear | 68 | 84 | 67 | 86 | 94 | 94 | 89 | |
| Tensile | 6.4 | 6.4 | 6.4 | 7.2 | 7.0 | 6.2 | 6.8 | |
| Bulk | 1.64 | 1.60 | 1.49 | 1.56 | 1.53 | 1.58 | 1.52 | |

TABLE II

PINE COOKS

| Cook No. | 9 | 10 | 11 | 12 | 13 | 14 |
|---|---|---|---|---|---|---|
| Prehydrolysis | None | None | | None | | |
| $H_2SO_4$, sol'n % | | | 1.0 | | 0.3 | 0.5 |
| Temp, °C. | | | 105 | | 120 | 120 |
| Time, min. | | | 45 | | 60 | 60 |
| Total solids, % | | | 1.2 | | 1.3 | 1.9 |
| Final pH | | | 1.4 | | 1.3 | 1.9 |
| Caustic Extraction | None | None | None | | | |
| NaOH, % on wood | | | | 1.5 | 1.5 | 1.9 |
| Temp, °C. | | | | 60 | 60 | 120 |
| Time, min. | | | | 60 | 60 | 60 |
| Liquor to wood | | | | 3.0 | 2.0 | 1.8 |
| Final pH | | | | 1.3 | 8.4 | 6.1 |
| Est. Solids Removal (% on O.D. wood) | | | | | | |
| prehydrolysis stage | | | | | 2.2 | 3.2 |
| extraction stage | | | | 1.7 | 2.5 | 2.9 |
| total | | | | 1.7 | 4.7 | 6.1 |
| Kraft Stage | | | | | | |
| AA, % | 17.2 | 18 | 15.5 | 14 | 14 | 14 |
| Max. temp., °C. | 170 | 171.5 | 170 | 170 | 170 | 170 |
| Time at max., min. | 90 | 90 | 90 | 90 | 90 | 90 |
| Residual AA, gpl | | | 9.6 | 8.5 | 6.0 | 9.5 |
| K Number | 21.3 | 2.8 | 23.8 | 27.0 | 23.7 | 22.2 |
| Total yield, % | 46.9 | 47.6 | 44.7 | 49.2 | 45.1 | 43.4 |
| Total rejects, % | 0.5 | 1.8 | 0.7 | 0.7 | 0.6 | 0.9 |
| Viscosity (cp) | 40.7 | 38.6 | 61.4 | 47.2 | 48.7 | 46.3 |
| V/K | 1.9 | 1.7 | 2.6 | 1.7 | 2.1 | 2.1 |
| Pentosans, % | 8.2 | 6.9 | 5.8 | 7.6 | 5.8 | 4.6 |
| Paper Properties 400 CSF | | | | | | |
| PFI revs | 8300 | 9100 | 6500 | 8300 | 7000 | 8000 |
| Burst | 66 | 70 | 63 | 65 | 63 | 61 |
| Tear | 218 | 212 | 233 | 228 | 225 | 217 |
| Tensile | 8.4 | 9.5 | 8.9 | 8.7 | 8.8 | 7.8 |
| Bulk | 1.71 | 1.72 | 1.60 | 1.78 | 1.68 | 1.68 |

Figure 4:
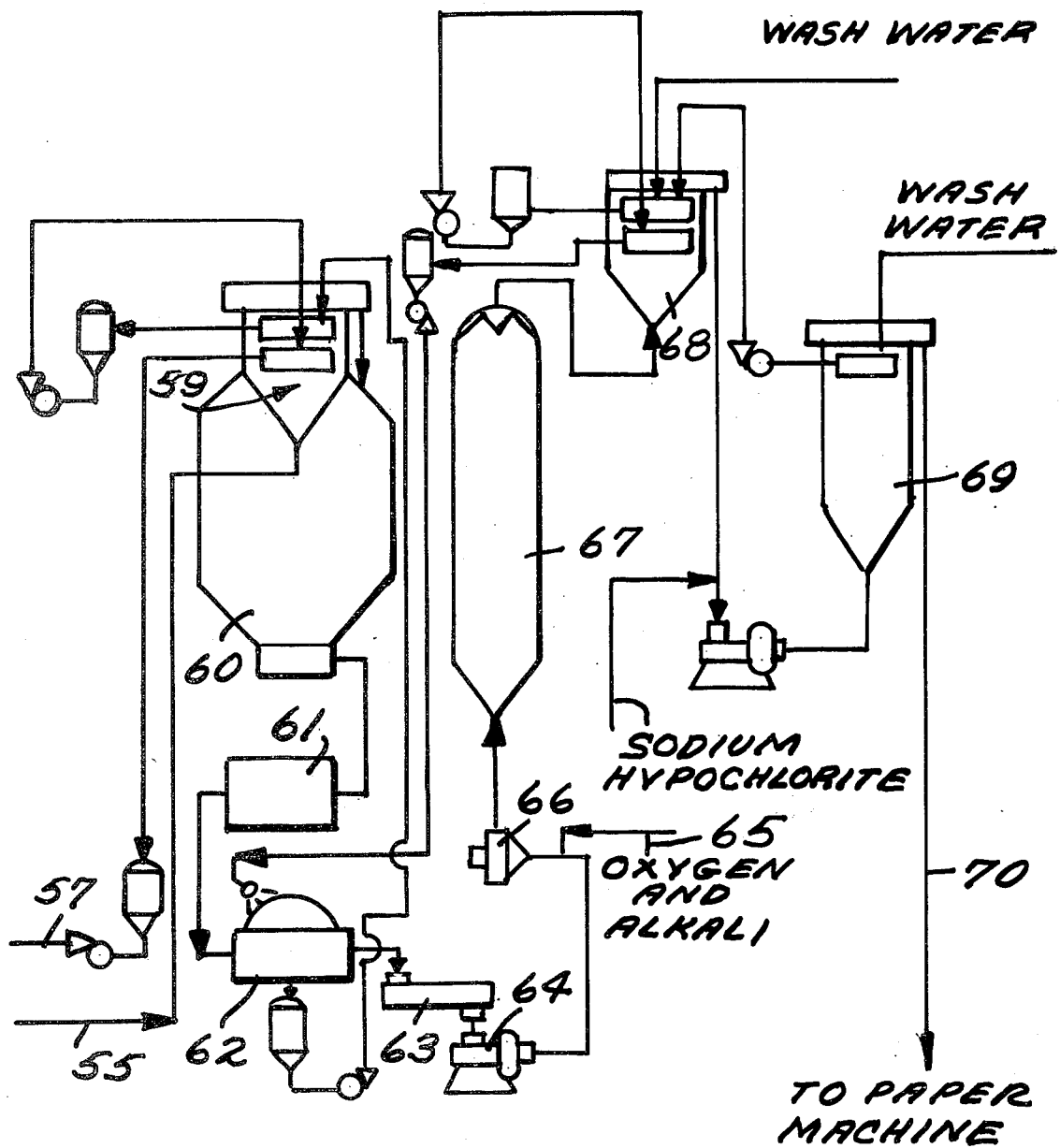
FIG. 4 is a schematic view of exemplary apparatus for the subsequent treatment of the kraft pulp discharged from the digester of FIG. 1, particularly relating to the oxygen delignification thereof.

Because of the high viscosity and low Kappa number of the kraft pulp produced after the cook when the acid prehydrolysis and caustic pre-extraction according to the invention are practiced, it is possible to carry out oxygen bleaching (or other oxygen delignification) to a lower Kappa number with fewer subsequent bleaching stages while still retaining appropriate pulp strength. This can be practiced utilizing the apparatus illustrated in FIG. 4 with the pulp withdrawal 55 and filtrate introduction 57 lines from the apparatus of FIG. 1 connected up to the corresponding lines in FIG. 4.

The pulp in line 55 may be passed to a conventional diffusion washer 59 and then introduced into storage tank 60, and may ultimately be passed through screen room 61 to decker washer 62, steam mixer 63, and high density pump 64 before having oxygen and alkali added thereto at line 65 just prior to high speed mixer 66. Oxygen bleaching or delignification then takes place in reactor vessel 67. A wide variety of conventional structures may be utilized for the described apparatus, and the pulp can be treated at medium consistency (e.g. about 8 to 12%, the consistency when discharged from the digester 45), or it may be reacted at lower high consistency. The delignified pulp then passes to second diffusion washer 68 and then to a hypochlorite bleaching vessel 69 or the like, and ultimately being discharged in line 70 to a paper machine. The number of subsequent bleaching stages is minimized, only the one stage 69 illustrated in FIG. 4 being necessary, and under some circumstances even that stage not being necessary.

The results in Tables III and IV indicate the results of practicing oxygen delignification and subsequent bleaching on the pulp obtained from some of the cooks in Tables I and II, and indicate advantages achievable according to the invention. For instance the difference in Kappa number for the same bleaching conditions for cooks 2 and 3 is a difference between 4.7 and 4.0. This could mean a difference of about 30% in the $ClO_2$ required to bleach to a brightness of 91+ in one stage. This could means the difference between requiring a subsequent perioxide stage or not. These bleaching results also indicate that the strength properties of the kraft pulp are maintainted through subsequent oxygen delignification procedures.

TABLE III

OXYGEN DELIGNIFICATION AND BLEACHING DATA FOR HARDWOOD

| Sample | 2 | | 7 | | 3 | |
|---|---|---|---|---|---|---|
| K No. (40 ml) | 15.2 | | 14.2 | | 15.5 | |
| Viscosity (0.5% CED) | 59.5 | | 66 | | 122 | |
| Oxygen Stage: | | | | | | |
| 100 psig, 22% Cs | | | | | | |
| NaOH, % | 1.8 | 3.5 | 3.8 | 2.5 | 3.5 | 2.9 |
| Temp., °C. | 115 | 120 | 125 | 115 | 120 | 115 |
| Time, min. | 60 | 60 | 60 | 60 | 60 | 50 |
| K. No. | 5.9 | 4.7 | 4.6 | 4.8 | 4.0 | 4.6 |
| Viscosity (cp) | 27.8 | 15.4 | 12.8 | 20.8 | 16.3 | 20.7 |
| V/K | 4.7 | 3.3 | 2.8 | 4.3 | 4.1 | 4.2 |
| Yield, % (est.) | | 93.6 | | 95.7 | 94.5 | |
| Brightness, SCAN | | 67.1 | | | | |
| $ClO_2$: 72° C., 150 min. | | | | | | |
| $ClO_2$, % | 1.45 | | 1.45 | | 1.15 | |
| NaOH Buffer, % | 0.73 | | 0.87 | | 0.52 | |
| Final pH | 4.2 | | 4.8 | | 4.6 | |
| Residual gpl, Av. Cl | nil | | 0.13 | | nil | |
| Brightness SCAN | 89.2 | | 90.8 | | 91.8 | |
| Viscosity (cp) | 13.1 | | 15.9 | | 14.4 | |
| Peroxide, 72° C., 90 min. | | | | | | |
| $H_2O_2$, % | 0.5 | | | | 0.5 | |
| Total Alkalinity, % | 0.8 | | | | 0.8 | |
| Final pH | 10.4 | | | | 10.4 | |
| Residual, % on Pulp | 0.17 | | | | 0.17 | |
| Brightness, SCAN | 92.3 | | | | 93.3 | |
| Viscosity (cp) | 12.1 | | | | 13.9 | |

TABLE IV

FIVE-STAGE BLEACHING DATA

| | | SAMPLE | | | |
|---|---|---|---|---|---|
| | | 11 Pine | 3 Hdwd | 9 Pine | 2 Hdwd. |
| Raw Stock | K No. (40 ml) | 23.9 | 15.5 | 21.3 | 15.2 |
| | Visc. (0.5%) | 61 | 122 | 40.7 | 59.5 |
| Dc D: 2 min. | Total avail. Cl. | 6.33 | 4.25 | 6.25 | 4.46 |
| Tl: 60 min. | % $ClO_2$ (as $ClO_2$) | 1.20 | 0.81 | 1.19 | 0.85 |
| 20° C., 3.5% Cs | % $Cl_2$ | 3.16 | 2.12 | 3.13 | 2.23 |

TABLE IV-continued

FIVE-STAGE BLEACHING DATA

| | | SAMPLE | | | |
|---|---|---|---|---|---|
| | | 11 Pine | 3 Hdwd | 9 Pine | 2 Hdwd. |
| 50% repl. | Resid. (g/l avail. Cl) | 0.01 | 0.01 | 0.02 | 0.05 |
| E 60 min. | % NaOH | 2.5 | 1.7 | 2.5 | 1.75 |
| 75° C., | Final pH | 12.2 | 12.1 | 12.1 | 12.1 |
| 10% Cs | K No. (25 ml) | 3.0 | 2.2 | 2.7 | 1.1 |
| | Visc. (0.5%) | 50. | (68) | 40.0 | 44.4 |
| | % Yield (est.) | 95.5 | 96.0 | 95.9 | 96.2 |
| D 150 min. | % $ClO_2$ | 0.85 | 0.67 | 0.78 | 0.50 |
| 72° C., | % NaOH (buffer) | 0.43 | 0.29 | 0.39 | 0.20 |
| 9% Cs | Final pH | (3.8) | 4.1 | 3.5 | 4.4 |
| | Resid. (g/l avail. Cl) | Trace | 0.08 | Trace | 0.11 |
| E 60 min. | % NaOH | 0.35 | 0.35 | 0.35 | 0.35 |
| 72° C., | Final pH | 11.4 | 11.3 | 11.6 | 11.5 |
| 10% Cs | | | | | |
| D 210 min. | % $ClO_2$ | 0.40 | 0.30 | 0.40 | 0.30 |
| 72° C., | % NaOH (buffer) | 0.12 | 0.09 | 0.12 | 0.08 |
| 9% Cs | Final pH | 4.4 | 5.1 | 4.3 | 5.1 |
| | Resid. (g/l avail. Cl) | 0.16 | 0.18 | 0.17 | 0.18 |
| | Brightness (SCAN) | 92.0 | 93.8 | 92.0 | 92.7 |
| | Viscosity (0.5) | 37 | 47 | 27.5 | 38.9 |
| | Total yield (est.) | 94.6 | 94.9 | | |

FIG. 2 illustrates exemplary apparatus for acting upon the hydrolysate withdrawn through line 40 to produce alcohol. The hydrolysate passes to mixing tank 70 where it is neutralized, passes to clarifier 71, and then to a conventional fermenter 72. The withdrawn "beer" from the fermenter 72 passes through a conventional yeast apparatus 73 through line 74 to distillation tower 75, steam being provided through line 76 for the distillation. A portion of the separated material from the yeast separation station 73 is passed through line 77 back to the fermenter 72, while another portion is passed through line 78 to a furnace 79 where it can be burned to produce steam. The steam can be used for addition at point 76, and/or to drive a turbine 80 or the like.

In the fermenter 71, appropriate microorganisms will be utilized to effect fermentation of the pentose and hexose sugars in the hydrolysate. Some exemplary publicly available microorganisms for that are: a microorganism located by Auburn University classified as AU-1-D3; Fusarium strains of fungus developed by Argone National Laboratory; and *Bacillus macerans* developed by The University of California at Berkeley, and Lawrence Berkeley Laboratory.

Figure 5:
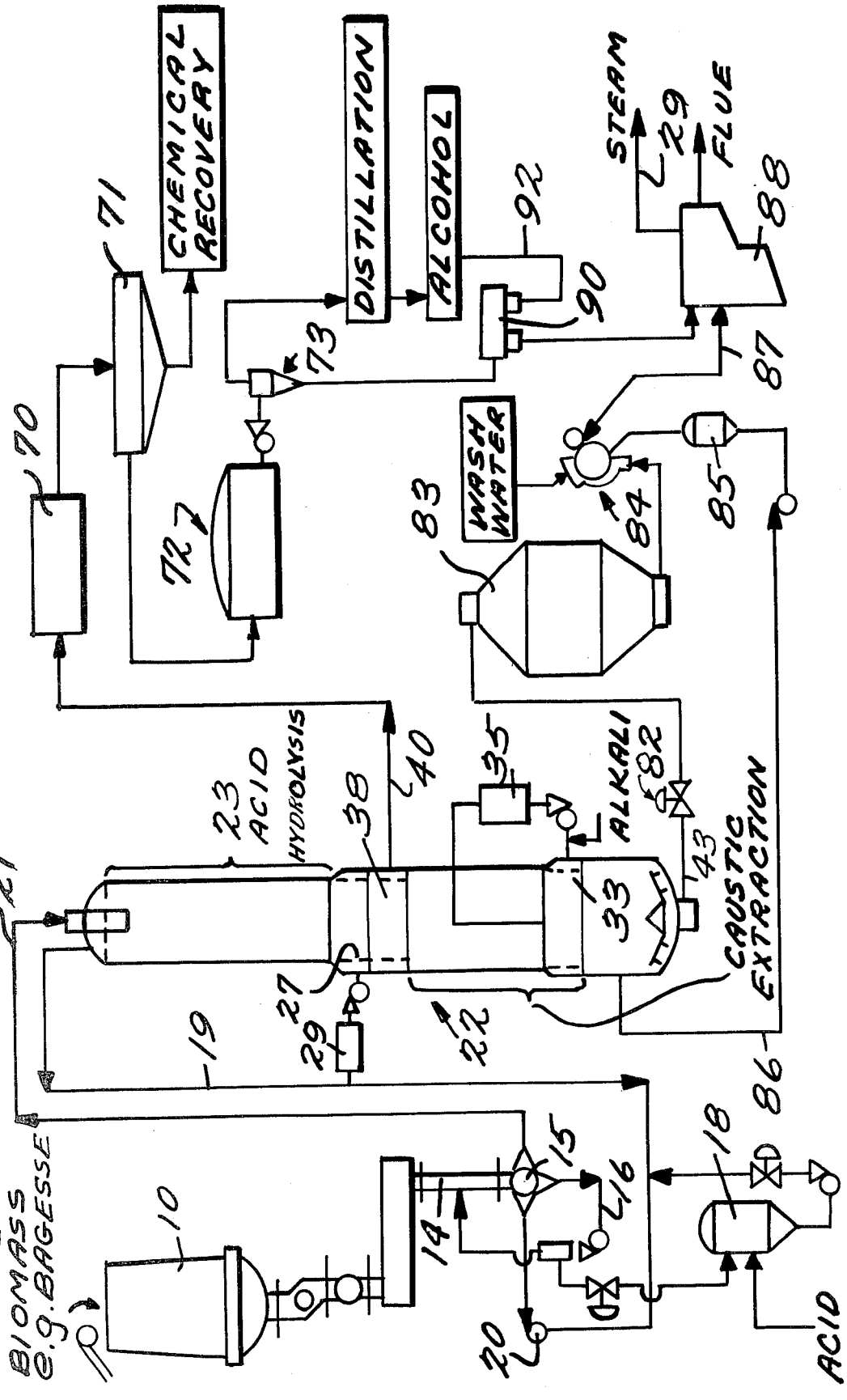
FIG. 5 is a schematic of exemplary apparatus for practicing a method aspect according to the present invention wherein a maximum amount of carbohydrate and lignin for the production of alcohol is removed from particlized and slurried biomass.

FIG. 5 illustrates apparatus utilizable in a method of producing alcohol according to the present invention from biomass that is not of high enough quality to produce kraft pulp. In this embodiment structures corresponding to those in other figures are indicated by like reference numerals. The biomass fed into the apparatus of FIG. 5 typically would be bagesse or like biomass containing carbohydrate and lignin, and the practice of the invention would effect hydrolysis of the hemicellulose in the biomass to effect separation of pentose and hexose sugars therefrom in a hydrolysate. The separation would be practiced so that the hydrolysate has insufficient furfural to substantially inhibit fermentation microorganism growth. For example, where microorganisms AU-1-D3 are utilized, the furfural concentration should be limited to about 0.18% (or less).

When utilizing the apparatus in FIG. 5, the desire is to maximize the amount of material removal in the hydrolysate, since the biomass discharged from vessel 22 will be burned, or otherwise used for purposes where a low quality material is acceptable. As illustrated in FIG. 5, the material discharged through line 43 passes through a blow valve 82, passes into a blow tank 83, and to a wash press 84. The filtrate from the wash press 84 passes to filtrate tank 85, and ultimately is returned to line 86 to the bottom of vessel 22. The dewatered biomass remaining passes through discharge line 87 to furnace 88, to be used in the production of steam or the like.

The acid hydrolysis and caustic extraction conditions when the apparatus of FIG. 5 is utilized may be slightly more severe than in the FIG. 1 embodiment since the purpose is to maximize material recovery in the hydrolysate and there is no concern for the strength of the material discharged through line 43. Thus, the acid hydrolysis may be practiced at a concentration of 0.3–2% $H_2SO_4$, or the equivalent, and a temperature of about 105°–135° C. The caustic extraction stage may be practiced with a concentration of 1.5–6% NaOH and at a temperature of 60°–120° C. The residence time in each case would be about 60 minutes, and the pressure conditions in the vessel 22 would be approximately the same as in the FIG. 1 embodiment. The removed hydrolysate in line 40 would be subjected to basically the same treatment as illustrated in FIG. 2, except that the discharge from the yeast apparatus 73 passes to a centrifuge 90, with the solids separated by the centrifuge passing through line 91 to the furnace 88, while the liquid passes through line 92 to be ultimately used for the wash water for press 84.

It will thus be seen that according to the present invention a method and apparatus have been provided which effect removal of high quality carbohydrate material (suitable for production of alcohol) from chips (particularly hardwood chips) with a minimum affect on final kraft pulp yield and strength (actually even increasing the pulp viscosity and tear strength). According to another aspect of the invention it will be seen that a maximum amount of high quality carbohydrate material may be removed from input biomass, particularly the pentose and hexose sugars, with the production of alcohol with a net energy benefit.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and devices.

What is claimed is:

1. A method of producing carbohydrate material and kraft pulp from a liquid slurry of comminuted cellulosic fiber material comprising the steps of continuously:
   (a) subjecting the liquid slurry of comminuted cellulosic fiber material to mild acid prehydrolysis, by subjecting said material to an acid concentration of, or equivalent to, about 0.2–0.5 percent $H_2SO_4$, and a temperature of about 120° C. or less;
   (b) subjecting the slurry of prehydrolized comminuted cellulosic fiber material to mild caustic pre-extraction, by subjecting said material to a caustic concentration of, or equivalent to, about 0.5–4.0 percent NaOH, and at a temperature of about 60°–90° C.;
   (c) removing hydrolysate, having carbohydrate material, released during the practice of steps (a) and (b) from the comminuted cellulosic material while continuously practicing steps (a) and (b); and
   (d) effecting kraft cooking of the prehydrolized, pre-extracted comminuted cellulosic fiber material to produce kraft pulp.

2. A method as recited in claim 1 wherein steps (a)–(c) are practiced so that the hydrolysate has a low enough furfural content so that it is useful as feed material for the production of alcohol.

3. A method as recited in claim 2 comprising the further steps of subjecting the hydrolysate to neutralization, clarification, fermentation, and distillation to produce alcohol.

4. A method as recited in claims 1, 2 or 3 wherein step (a) is practiced by providing a concurrent flow of the slurry of comminuted cellulosic fiber material and acid.

5. A method as recited in claim 4 wherein step (c) is practiced by providing a countercurrent flow of the slurry of comminuted cellulosic fiber material and caustic.

6. A method as recited in claims 1, 2 or 3 wherein step (c) is practiced by providing a countercurrent flow of the slurry of comminuted cellulosic fiber material and caustic.

7. A method as recited in claim 1 comprising the further step (e) of effecting oxygen delignification of the kraft pulp, and wherein steps (a)–(e) are practiced so that the delignified kraft pulp produced has a lower Kappa number than such pulp produced from the same comminuted cellulosic fiber material and under substantially identical kraft cooking and oxygen delignification conditions but without prehydrolysis and pre-extraction.

8. A method as recited in claim 7 wherein the cellulosic fiber material is chips or sawdust of hardwood.

9. A method as recited in claim 7 wherein steps (a)–(c) are practiced so that the hydrolysate has a low enough furfural content so that it is useful as feed material for the production of alcohol.

10. A method as recited in claims 1, 2 or 7 wherein steps (a)–(c) are practiced in a first vertical vessel, and step (d) is practiced in a second vertical vessel, distinct from the first vessel.

11. A method of treating cellulosic fiber material utilizing a first vessel and a separate second vessel, said method comprising the steps of continuously:
   (a) feeding comminuted cellulosic fiber material entrained in treatment liquid to a top portion of the first vessel;
   (b) effecting mild acid prehydrolysis in an upper portion of the first vessel, by subjecting the material to an acid concentration of, or equivalent to, about 0.2–0.5 percent $H_2SO_4$, and a temperature of about 120° C. or less;
   (c) effecting mild caustic pre-extraction in a lower portion of the first vessel, by subjecting the material to a caustic concentration of, or equivalent to, about 0.5–4.0 percent NaOH, and at a temperature of about 60°–90° C.;
   (d) withdrawing hydrolysate from a screen of the first vessel;

(e) withdrawing liquid from a top portion of the first vessel to feed it back to entrain further feed comminuted cellulosic fiber material;

(f) withdrawing prehydrolized and pre-extracted fiber material from the bottom of the first vessel;

(g) feeding the material withdrawn from the bottom of the first vessel to the top of the second vessel;

(h) effecting sulfate digestion of the fiber material in the second vessel;

(i) withdrawing liquid from the top portion of the second vessel and returning it to the bottom of the first vessel; and (j) withdrawing pulp from the bottom of the second vessel.

12. A method as recited in claim 11 wherein the acid prehydrolysis in the first vessel is practiced with concurrent flow between the acid and fiber material being treated.

13. A method as recited in claim 12 wherein the caustic pre-extraction is practiced with a countercurrent flow of caustic to the direction of flow of fiber material; and wherein the hydrolysate is withdrawn through a screen at a central vertical position of the first vessel.

14. A method as recited in claims 11 or 12 comprising the further steps of: withdrawing liquid from a position along the acid prehydrolysis portion of the first vessel; heating the withdrawn liquid; adding acid to the withdrawn liquid to effect the desired acid concentration in the prehydrolysis zone; and returning the withdrawn liquid, after heating and acid addition, to the acid prehydrolysis zone of the first vessel.

15. A method as recited in claim 12 comprising the further step of: effecting acid addition to the return line from the top of the first vessel to entrain further fiber material prior to the entrainment of further fiber material therewith, the acid addition providing the proper acid concentration for the acid prehydrolysis zone in the first vessel.

16. A method as recited in claim 11 wherein said mild caustic pre-extraction is practiced by withdrawing liquid through a screen at a bottom portion of the pre-extraction zone of the first vessel; cooling the withdrawn liquid; adding sufficient alkali to the withdrawn liquid to maintain the caustic concentration in the pre-extraction zone at a desired level; and introducing the cooled, alkali-added liquid to a central portion of the first vessel in the caustic pre-extraction zone.

17. A method as recited in claim 16 wherein said central portion for re-introduction of liquid into the caustic pre-extraction zone is adjacent the bottom of the caustic pre-extraction zone, and wherein the introduced caustic flows countercurrently to the material flowing downwardly in the first vessel.

18. A method as recited in claim 11 comprising the further steps of: adding white liquor to the return line from the top of the second vessel to the bottom of the first vessel, and heating the liquid in the return line from the top of the second vessel to the first vessel.

19. A method as recited in claim 11 wherein the method steps are practiced so that the pulp discharged from the second vessel is sulphate pulp having a substantially higher viscosity than the same pulp produced from the same comminuted cellulosic fiber material and under substantially identical sulfate processing conditions but without prehydrolysis and pre-extraction; and wherein the withdrawn hydrolysate is subjected to the further steps of: neutralization; clarification; fermentation; and distillation to produce alcohol.

20. A method as recited in claim 19 comprising the further step (k) of effecting oxygen delignification of the sulphate pulp, and wherein steps (a)–(k) are practiced so that the delignified sulphate pulp produced has a lower Kappa number than such pulp produced from the same comminuted cellulosic fiber material and under substantially identical sulphate cooking and oxygen delignification conditions but without prehydrolysis and pre-extraction.

* * * * *